United States Patent
Rajaiah et al.

(10) Patent No.: US 8,623,388 B2
(45) Date of Patent: Jan. 7, 2014

(54) DENTURE CARE COMPOSITION

(75) Inventors: Jayanth Rajaiah, Loveland, OH (US); Arif Ali Baig, Mason, OH (US); Robert Scott Leonard, Fairfield, OH (US); Elizabeth Anne Wilder, West Chester, OH (US); Franco Silva Medeiros, Loveland, OH (US); Luisa Navarro Cerda, Cincinnati, OH (US); Steven Daryl Smith, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 231 days.

(21) Appl. No.: 12/911,112

(22) Filed: Oct. 25, 2010

(65) Prior Publication Data

US 2011/0104219 A1  May 5, 2011

Related U.S. Application Data

(60) Provisional application No. 61/255,926, filed on Oct. 29, 2009.

(51) Int. Cl.
| | | |
|---|---|---|
| *A61K 8/00* | (2006.01) |
| *A61K 9/00* | (2006.01) |
| *A61P 29/00* | (2006.01) |
| *A61P 31/10* | (2006.01) |
| *A61P 23/00* | (2006.01) |
| *A61P 31/12* | (2006.01) |
| *A61P 39/06* | (2006.01) |
| *A61P 3/02* | (2006.01) |
| *A61P 31/00* | (2006.01) |
| *A61Q 11/02* | (2006.01) |

(52) U.S. Cl.
USPC .............................. 424/401; 424/49; 424/484

(58) Field of Classification Search
USPC .......................................................... 424/49
See application file for complete search history.

(56) References Cited

U.S. PATENT DOCUMENTS

| 5,605,676 A | 2/1997 | Gaffar et al. |
| 2005/0281757 A1* | 12/2005 | Ibrahim et al. .................. 424/49 |
| 2006/0177384 A1 | 8/2006 | Brown et al. |

* cited by examiner

*Primary Examiner* — Walter Webb
(74) *Attorney, Agent, or Firm* — Angela K. Haughey; Kathleen Y. Carter; James E. Oehlenschlager

(57) ABSTRACT

A denture care composition comprising one or more denture care actives and one or more water insoluble carriers, wherein the composition is bioerodible, not a denture adhesive, and substantially free of polybutene with a molecular weight of about 300 to about 3000 when the composition is not an article, and is applied to dentures.

22 Claims, No Drawings

DENTURE CARE COMPOSITION

CROSS REFERENCE OF RELATED APPLICATION

This application claims the benefit of provisional application Ser. No. 61/255,926, filed on Oct. 29, 2009, which is incorporated by reference in its entirety herein.

FIELD OF THE INVENTION

The present invention relates to a denture care composition comprising one or more denture care actives and one or more water insoluble carriers, wherein the composition is not a denture adhesive.

BACKGROUND OF THE INVENTION

In the United States, there are approximately 50 million people who wear dentures. These people have a higher-than-normal need to take care of their breath and to protect any remaining natural teeth. It is known that denture care products can deliver various denture care actives to the surface of the artificial teeth, thus providing both therapeutic and cosmetic benefits to consumers. For example, effervescent denture cleansing tablets, which require soaking the artificial teeth for a period of time, work to remove plaque and debris that have built up on the denture or plate. But such denture care products typically do not maintain the denture care actives in the oral cavity long enough to optimally enhance or prolong the therapeutic, prophylactic and/or cosmetic benefits provided by the actives, or they do not maintain a high concentration of the active against the denture surface.

U.S. Pat. No. 6,500,406, issued Dec. 31, 2002 to Rajaiah, et al., the substance of which is incorporated herein by reference, discloses a denture care composition that provides prolonged release of denture care actives. The Rajaiah patent discloses use of polybutene, which, while extremely substantive, can also be difficult to process, difficult and messy for consumers to handle, and expensive. Therefore, there remains a continuing need for easy-to-produce and easy-to-handle denture care compositions that can cheaply deliver denture care actives, such as breath-freshening ingredients or antimicrobials, over prolonged periods of time.

SUMMARY OF THE INVENTION

The present invention relates to a denture care composition comprising one or more denture care actives and one or more water insoluble carriers, wherein the composition is bioerodible, not a denture adhesive, and substantially free of polybutene with a molecular weight of about 300 to about 3000 when the composition is not an article, and is applied to dentures.

DETAILED DESCRIPTION OF THE INVENTION

Definitions

The term "dentures" as used herein, is meant to include dentures, dental plates, bridges, artificial teeth and other surfaces of dental appliances that are temporarily fixed within the oral cavity and that are typically removed from the oral cavity for cleaning.

The abbreviation "cm" as used herein, means centimeter. The abbreviation "mm" as used herein, means millimeter. The abbreviation "g" as used herein, means gram. The abbreviation "P" as used herein, Pascal. The abbreviation "s" as used herein means second. The abbreviation "Ps" as used herein means Pascal-second. The abbreviation "oz" as used herein, means ounce.

The term "bioerodible" as used herein means that the composition, when exposed to excess of water or saliva, will erode over time due to physical and/or chemical action. The time necessary to erode the composition can be any length of time from instantaneous to five days, in one embodiment the time to erode is from about 1 to about 3 days. The composition may erode completely or substantially; however, ultimately the composition will lose its original form and/or integrity. For example, in one embodiment, after application and use for at least about 24 hours in the oral cavity, the composition will not have sufficient product integrity to easily separate or peel, in its original form, from the denture or oral surface. In another embodiment, the composition bioerodes such that no portion of the composition remains on the denture or mouth after the composition has been used in the oral cavity for about 24 hours. In another embodiment some portion or residue from the composition remains on the denture or oral surface after removing the denture from the oral cavity; however, this portion or residue from the composition can be cleaned by brushing away with a toothbrush, but not easily separated from the denture.

The term "denture adhesive" as used herein, refers to compositions that improve denture retention and comfort. Denture retention may be measured by the maximum incisal bite force recorded about 8 hours after application of the composition onto the denture. Procedures to measure maximum incisal bite force are described in the publication "Effect of denture adhesive on the retention and stability of maxillary dentures" by Joseph E. Grasso et al. in The Journal of Prosthetic Dentistry October 1994 pages 399-405. This publication also states, "The use of an adhesive enabled patients to generate significantly greater levels of incisal bite force 8 hours after application. These increases were on the order of 20 Newtons from approximately 35 N at baseline to a maximum of 54 N at 8 hours after application."

The term "safe and effective amount" as used herein, means an amount of an agent (e.g., anti-calculus agent) high enough to significantly improve the condition to be treated, but low enough to avoid serious side effects (at a reasonable benefit/risk ratio), within the scope of sound medical/dental judgment. The safe and effective amount of an agent (e.g., anti-calculus agent) may vary with the particular condition being treated, the age and physical condition of the patient being treated, the severity of the condition, the duration of treatment, the nature of concurrent therapy, the specific form of the source employed, and the particular vehicle from which the agent is applied.

The term "article" as used herein, refers to articles designed to fit, conform and adhere to contoured surfaces, such as a denture. The articles herein are substantially solid prior to use and can be picked up manually in substantially one piece and positioned on the denture.

The term "flexible" or "flexible article" as used herein means that a 0.67 mm thick piece of the article may be wrapped 180 degrees around a solid cylinder of 1 cm diameter without cracking upon visual observation.

The term "toxicologically-acceptable" as used herein, is used to describe materials that are suitable in their toxicity profile for administration to humans and/or animals.

The term "non-aqueous" as used herein, means that the composition does not contain added water but may contain water that is included in another component as supplied commercially by the manufacturer.

The term "water insoluble" as used herein refers to a material that, when exposed to an excess of water, does not dissolve, but may disperse to varying degrees. In some embodiments the term "water insoluble" refers to a material that is less than about 10%, 5%, 2%, or 1% soluble in water.

The term "viscosity index improver" as used herein refers to a material which makes the viscosity and/or rheology of a material into which it is incorporated more stable as its temperature is increased over a defined range. In the case of denture care products, the defined range is between about 25° C. and about 60° C.

Unless otherwise noted, the term "melting point" as used herein refers to the Drop Melting Point which is the temperature at which the material becomes sufficiently fluid to drop from the thermometer used in making the determination under prescribed conditions as listed in ASTM D-127. ASTM D-3954 is an alternate way to measure melting point.

Unless otherwise noted, the term "derivative" as used herein refers to when the primary polymeric backbone is left unchanged, but the side groups/chains and/or end groups are changed.

As used herein, the term "silicone" refers to siloxane polymers based on a structure of alternate silicon and oxygen atoms with various organic radicals attached to the silicon.

The term "thermoplastic" as used herein refers to a material that melts, softens, becomes more flexible, extrudable, deformable, shapeable, moldable, flowable, processable, and/or changes rheology when exposed to heat. In one embodiment the material generally solidifies, hardens, and/or substantially returns to its original condition, when subsequently cooled.

The term "mucoadhesive" or "bioadhesive" as used herein refers to the phenomenon where a natural or synthetic substance applied to a wet mucosal epithelium adheres, usually creating a new interface, to the mucous layer. (*CRC Critical Review in Ther. Drug Carrier*, Vol. 5, Issue 1, p. 21 (1988)). Generally, mucoadhesion can be achieved via physical or chemical processes, or both. One such mechanism is described in *Journal of Controlled Release*, Vol. 2, p 257 (1982) and *Journal of Controlled Release*, Vol. 18 (1992) p. 249. The above references are incorporated by reference herein in their entirety.

The term "unit dose form" refers to physically discrete units suitable as unitary dosages for human subjects and other mammals, each containing a predetermined quantity of active material calculated to produce the desired therapeutic effect.

The term "viscosity", as used herein, refers to the internal resistance to flow or deformation of a material. This can be measured by the ratio of shearing stress to rate of shear; and in some embodiments where this ratio is not suitably measured, suitable rheological parameters such as loss modulus G" or storage modulus G' can be measured.

The term "container" as used herein, means a jar, cup, can, tube, aerosol can, tub, pump, bottle or any other liquid holding or dispensing means.

The terms "tartar" and "calculus" are used interchangeably and refer to mineralized dental plaque biofilms.

The term "molecular weight" as used herein, is reported as a number average, determined using gel permeation chromatography.

The term "sensate" as used herein refers to a material in which its predominant effect in the oral cavity is to impart a sensation, for example, a warming, cooling, and/or tingling sensation.

The term "flavor" as used here refers to a material in which its predominant effect in the oral cavity is to impart a taste, excluding sweeteners.

The term "sweetener" as used herein refers to a material in which its predominant effect in the oral cavity is to impart a sweet taste.

The term "R1" as used herein refers to the ratio "weight of sensates/weight of flavors" in the composition.

The term "R2" as used herein refers to the ratio "weight of flavors/weight of sweeteners" in the composition The term "R3" as used herein refers to the ratio "weight of sensates/weight of sweeteners" in the composition.

The term "R4" as used herein refers to the ratio "(weight of sensates+weight of flavors)/weight of Sweeteners)" in the composition.

All percentages and ratios herein are by weight of total composition, unless otherwise indicated.

All measurements referred to herein are made at about 25° C. unless otherwise specified.

Denture Care Composition

The present invention is a composition that is able to deliver one or more denture care actives over prolonged periods of time to denture wearers when used on the denture in the oral cavity, or to the denture when used outside of the oral cavity. Denture wearers in general can have a higher perceived need for breath freshening, leading to a heightened need for long-acting denture care actives, such as breath fresheners. Partial denture wearers can also have an increased risk of losing adjacent natural teeth and thus have an additional reason to receive long-acting denture care actives, such as antimicrobials. So while these vulnerabilities can put denture wearers at a disadvantage versus dentate people, denture wearers do have at least one advantage in that their dentures provide a built-in platform onto which various actives may be deposited and subsequently released over several hours.

Without being bound by theory, the present invention keys on the insight that denture surfaces are fairly hydrophobic compared to the mucosal surfaces of the mouth. As such, water insoluble materials such as petrolatum, waxes, oils, etc., can adhere well to the denture and resist being eroded in the saliva. Furthermore, if the water insoluble material comprises actives, such as breath-freshening ingredients, coolants, or antimicrobials, these agents can release slowly over time into the mouth, for much longer times than achievable through water soluble products such as mouth rinses and dentifrices.

To be clear, the present invention is a denture care composition that is not a denture adhesive composition. It is not designed to and does not significantly improve denture retention and comfort in the oral cavity. The surprising discovery of the present invention is that certain water insoluble materials, some even that are typically used as components in traditional denture adhesive compositions, when used even without the mucoadhesive component of denture adhesive compositions, become a different type of composition, a composition that sticks and stays on surfaces that are not wet mucosal surfaces. For example, unlike a denture adhesive, these compositions stick to the denture, but not at all (or minimally) to the wet mucosal tissue. That is, rather than being a composition for adhering one thing to another (a denture to the oral cavity), the composition is cohesive, sustaining itself for extended periods of time.

In some embodiments, the present invention is substantially free of or does not comprise an effective amount of a component or components that would significantly improve the retention of the denture in the oral cavity. In some embodiments, the composition is substantially free of mucoadhesive components, that is, substantially free of any component or components that would adhere to wet mucosal surfaces.

Based on the insight discussed above, another surprising and unexpected result discovered by the inventors of the present invention is that extreme substantivity, such as that of a polybutene, is not necessary to achieve long-lasting delivery of denture care actives. Therefore, compositions of the present invention are substantially free of polybutene with a molecular weight of about 300 to about 3000 when the composition is not an article. It is now discovered that many water insoluble materials, such as petrolatum and waxes, even when used without traditional mucoadhesive materials, provide sufficient substantivity to dentures, that is, they will remain cohesive and stick to the dentures for a long enough time to allow better and more effective delivery of denture care actives.

So while the composition does not significantly improve retention by adhering the denture in or to the oral cavity, the composition itself adheres to the surfaces of the denture for extensive periods of time. While adhering to the surfaces of the denture, the present compositions can release the denture care actives. In some embodiments, the composition will remain in the oral cavity and deliver denture care actives from application to about 1 hour, from application to about 2 hours, from application to about 3 hours, from application to about 4 hours, from application to about 6 hours, from application to about 8 hours, or from application to more than about 8 hours.

The present invention can be a cream, paste, gel, liquid, strip, wafer, article, or any other suitable form.

Denture Care Actives

The denture care compositions of the present invention may contain a denture care active where, upon directed use, the benefit sought by the wearer is promoted without detriment to the oral cavity or denture. Examples of the dental conditions these actives address include, but are not limited to, appearance and structural changes to teeth, treatment and prevention of plaque, calculus, cavities in remaining natural teeth, inflamed and/or bleeding gums, gingivitis, fungal infections such as candida, mucosal wounds, lesions, ulcers, aphthous ulcers, cold sores, tooth abscesses, and the elimination of mouth malodor resulting from the conditions above and other causes such as microbial proliferation.

Suitable denture care active ingredients include any material that is generally considered safe for use in the oral cavity and that provides changes to the overall appearance, feeling, smell, taste, sensorial attributes, and/or health of the oral cavity. Examples of denture care actives also include flavors, sensates, and/or sweeteners. The level of denture care active in the present invention is generally, unless otherwise noted, from about 0.001% to about 90%, in one embodiment from about 0.01% to about 50%, in another embodiment from about 0.1% to about 30%, by weight of the composition. Where the denture care actives are in particulate form, a suitable particle size for use in the present invention is from about 0.01 microns to about 1000 microns, in one embodiment from about 0.1 microns to 500 microns, in another embodiment from about 1 to about 100 microns. The denture care composition of the present invention may include many of the denture care actives previously disclosed in the art. The following is a non-limiting list of denture care actives that may be used in the present invention.

The present compositions may comprise at least one anti-calculus (i.e. anti-tartar) agent, present at a level from about 0.001% to about 50%, by weight of the composition, in another embodiment from about 0.01% to about 25%, and in yet another embodiment from about 0.1 to about 15%. The anti-calculus agent should be essentially compatible with the other components of the invention. The anti-calculus agent may be selected from the group consisting of polyphosphates (including pyrophosphates) and salts thereof; polyamino propane sulfonic acid (AMPS) and salts thereof; polyolefin sulfonates and salts thereof; polyvinyl phosphates and salts thereof; polyolefin phosphates and salts thereof; diphosphonates and salts thereof; phosphonoalkane carboxylic acid and salts thereof; polyphosphonates and salts thereof; polyvinyl phosphonates and salts thereof; polyolefin phosphonates and salts thereof; polypeptides; and mixtures thereof. In one embodiment, the salts are alkali metal salts. Polyphosphates are generally employed as their wholly or partially neutralized water-soluble alkali metal salts such as potassium, sodium, ammonium salts, and mixtures thereof. The inorganic polyphosphate salts include alkali metal (e.g. sodium) tripolyphosphate, tetrapolyphosphate, dialkyl metal (e.g. disodium) diacid, trialkyl metal (e.g. trisodium) monoacid, potassium hydrogen phosphate, sodium hydrogen phosphate, and alkali metal (e.g. sodium) hexametaphosphate, and mixtures thereof. Polyphosphates larger than tetrapolyphosphate usually occur as amorphous glassy materials. In one embodiment the polyphosphates are those manufactured by FMC Corporation, which are commercially known as Sodaphos (n≈6), Hexaphos (n≈13), and Glass H (n≈21, sodium hexametaphosphate), and mixtures thereof.

Fluoride ion sources are known for use in denture care compositions as anti-caries agents for remaining natural teeth and may optionally be incorporated within the present invention. Application of fluoride ions to the dental enamel of natural teeth serves to protect those teeth against decay. A wide variety of fluoride ion-yielding materials can be employed as sources of soluble fluoride in the instant compositions. Examples of suitable fluoride ion-yielding materials are found in Briner, et al., U.S. Pat. No. 3,535,421 and Widder, et al., U.S. Pat. No. 3,678,154. Preferred fluoride ion sources for use herein include sodium fluoride, potassium fluoride, stannous fluoride, mono fluoro phosphate (MFP), and ammonium fluoride. In one embodiment sodium fluoride is the fluoride ion source. The instant invention may provide from about 5 ppm to 10,000 ppm, in one embodiment from about 100 to 3000 ppm, of fluoride ions in the total composition.

The compositions of the present invention may include a stannous ion source as a denture care active. The stannous ions may be provided from stannous fluoride and/or other stannous salts. Stannous fluoride has been found to help in the reduction of gingivitis, plaque, sensitivity, and in improved breath benefits. The stannous ions provided in a denture care composition will provide efficacy to a subject using the composition. Although efficacy could include benefits other than the reduction in gingivitis, efficacy is defined as a noticeable amount of reduction in in situ plaque metabolism. Other stannous salts include organic stannous carboxylates, such as stannous acetate, stannous gluconate, stannous oxalate, stannous malonate, stannous citrate, stannous ethylene glycoxide, stannous formate, stannous sulfate, stannous lactate, stannous tartrate, and the like. Other stannous ion sources include, stannous halides such as stannous chlorides, stannous bromide, stannous iodide and stannous chloride dihydride. In one embodiment the stannous ion source is stannous fluoride in another embodiment, stannous chloride dihydrate. The combined stannous salts may be present in an amount of from about 0.01% to about 11%, by weight of the compositions. The stannous salts may typically be present in an amount of from about 0.1% to about 7%, in one embodiment from about 1% to about 5%, and in yet another embodiment from about 1.5% to about 3%, by weight of the composition.

Anti-microbial agents may also be present as a denture care active in the denture care composition of the present invention. Such agents may include, but are not limited to: 5-chloro-2-(2,4-dichlorophenoxy)-phenol, commonly referred to as Triclosan, and described in *The Merck Index,* 11th ed. (1989), pp. 1529 (entry no. 9573) in U.S. Pat. No. 3,506,720, and in European Patent Application No. 0,251,591 of Beecham Group, PLC; 8-hydroxyquinoline and its salts; copper II compounds, including, but not limited to, copper(II) chloride, copper(II) sulfate, copper(II) acetate, copper(II) fluoride and copper(II) hydroxide; phthalic acid and its salts including, but not limited to those disclosed in U.S. Pat. No. 4,994,262, preferably magnesium monopotassium phthalate; chlorhexidine; alexidine; hexetidine; sanguinarine; benzalkonium chloride; salicylanilide; domiphen bromide; cetylpyridinium chloride (CPC); tetradecylpyridinium chloride (TPC); N-tetradecyl-4-ethylpyridinium chloride (TDEPC); octenidine; iodine; sulfonamides; bisbiguanides; phenolics; delmopinol, octapinol, and other piperidino derivatives; nicin preparations; zinc/stannous ion agents; nystatin; grapefruit extracts; apple extracts; thyme oil; thymol; antibiotics such as augmentin, amoxicillin, tetracycline, doxycycline, minocycline, metronidazole, neomycin, kanamycin, and clindamycin; analogs and salts of the above; essential oils including thymol, geraniol, carvacrol, citral, hinokitiol, eucalyptol, catechol (particularly 4-allyl catechol) and mixtures thereof; methyl salicylate; hydrogen peroxide; metal salts of chlorite; xylitol; decapinol; delmopinol; and mixtures of all of the above.

The present invention does not comprise effective amounts of an antibacterial seed or pulp extract from the Citrus plant family, the Vitis plant family, and mixtures thereof. In some embodiments, there may be no effective amount of an antimycotic drug. In some embodiments, the composition may not form a film.

The compositions of the present invention may include an anti-plaque agent such as stannous salts, copper salts, xylitol, decapinol, delmopinol, strontium salts, magnesium salts or a dimethicone copolyol. The dimethicone copolyol is selected from C12 to C20 alkyl dimethicone copolyols and mixtures thereof. In one embodiment the dimethicone copolyol is cetyl dimethicone copolyol marketed under the Trade Name Abil EM90. The dimethicone copolyol may be present in a level of from about 0.001% to about 25%, in one embodiment from about 0.01% to about 5% and in another embodiment from about 0.1% to about 1.5% by weight of the composition.

Anti-inflammatory agents can also be present in the compositions of the present invention. Such agents may include, but are not limited to, non-steroidal anti-inflammatory agents oxicams, salicylates, propoionic acids, acetic acids and fenamates. Such NSAIDs include but are not limited to Ketorolac, flurbiprofen, ibuprofen, naproxen, indomethacin, diclofenac, etodolac, indomethacin, sulindac, tolmetin, ketoprofen, fenoprofen, piroxicam, nabumetone, aspirin, diflunisal, meclofenamate, mefenamic acid, oxyphenbutazone, phenylbutazone and acetaminophen. Use of NSAIDs such as Ketorolac are claimed in U.S. Pat. No. 5,626,838, issued May 6, 1997. Suitable steroidal anti-inflammatory agents include corticosteroids, such as fluccinolone, and hydrocortisone.

Nutrients may improve the condition of the oral cavity and can be included in the compositions of the present invention. Nutrients include minerals, vitamins, oral nutritional supplements, enteral nutritional supplements, and mixtures thereof. Useful minerals include calcium, phosphorus, zinc, manganese, potassium, and mixtures thereof. Vitamins can be included with minerals or used independently. Suitable vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Minerals, vitamins, oral nutritional supplements and enteral nutritional supplements are described in more detail in *Drug Facts and Comparisons* (loose leaf drug information service), Wolters Kluer Company, St. Louis, Mo., ©1997, pps. 3-17 and 54-57.

A whitening agent may be included in the present invention. The actives suitable for whitening are selected from the group consisting of peroxides, metal chlorites, perborates, percarbonates, peroxyacids, persulfates such as oxones, and combinations thereof. Suitable peroxide compounds include hydrogen peroxide, urea peroxide, calcium peroxide, carbamide peroxide, and mixtures thereof. In one embodiment the peroxide compound is carbamide peroxide. Suitable metal chlorites include calcium chlorite, barium chlorite, magnesium chlorite, lithium chlorite, sodium chlorite, and potassium chlorite. Additional whitening actives may be hypochlorite and chlorine dioxide. In one embodiment the chlorite is sodium chlorite. In another embodiment the percarbonate is sodium percarbonate. This may be used in compositions of the present invention at levels from about 0.1% to about 35%, in one embodiment from about 1% to about 25% and in another embodiment from about 5% to about 10% of the composition.

Antioxidants are generally recognized as useful in denture care compositions. Antioxidants are disclosed in texts such as Cadenas and Packer, *The Handbook of Antioxidants,* © 1996 by Marcel Dekker, Inc. Antioxidants that may be included in the present invention include, but are not limited to Vitamin E, ascorbic acid, Uric acid, carotenoids, Vitamin A, flavonoids and polyphenols, herbal antioxidants, melatonin, aminoindoles, lipoic acids and mixtures thereof.

Antiviral actives useful in the present invention include any known actives that are routinely used to treat viral infections. Such antiviral actives include, but are not limited to: phosphonoformic acid; cyosine derivatives; purine anaglogues, such as adenosine, guanosine and inosine analogues; pyrimidine bases, such as citidine and thymidine; amantadines; rimantadine HCl; ribavirin; zanamivir; oseltamivir phosphate; trifluridine; heterocyclic dyes; acyclovir; famciclovir; valacyclovir, cidofovir; ganciclovir; levimisole; idoxuridine; lipophilic β-ketones; and thiosemicarbazones. These antiviral actives are described in *Drug Facts and Comparisons* (loose-leaf drug information service), Wolters Kluwer Company, St. Louis, Mo., ©2001, pp. 1400-1423(b), and in *Kirk-Othmer, Encyclopedia of Chemical Technology*, Fourth Edition, Volume 3, Wiley-Interscience Publishers (1992), pp. 576-607, both incorporated herein by reference in their entirety. Specific examples include antiviral actives disclosed in U.S. Pat. No. 5,747,070, to Majeti, incorporated herein by reference in its entirety. Said patent discloses the use of stannous salts to control viruses.

Anti-fungal agents can also be included in the denture care compositions of the present invention. Anti-fungals are agents that destroy or inhibit the growth of fungi. Anti-fungal agents useful in the present invention are those drugs for systemic mycoses or drugs for mucocutaneuos infections. Suitable antifungals include but are not limited to nystatin, miconazole, econazole nitrate, clotrimazole, and flucytosine. In one embodiment the antifungal agent is nystatin.

Anti-pain or desensitizing agents can also be present in the denture compositions of the present invention. Analgesics are agents that relieve pain by acting centrally to elevate pain threshold without disturbing consciousness or altering other sensory modalities. Such agents may include, but are not limited to, strontium chloride, potassium nitrate, sodium nitrate, sodium fluoride, acetanilide, phenacetin, acertophan, thiorphan, spiradoline, aspirin, codeine, thebaine, levorphenol, hydromorphone, oxymorphone, phenazocine, fentanyl, buprenorphine, butaphanol, nalbuphine, pentazocine, natural herbs such as gall nut, Asarum, Cubebin, Galanga, scutellaria, Liangmianzhen, Baizhi, etc. Anesthetic agents, or topical analgesics, such as acetaminophen, sodium salicylate, trolamine salicylate, lidocaine and benzocaine may also be present. These analgesic actives are described in detail in *Kirk-Othmer, Encyclopedia of Chemical Technology*, Fourth Edition, Volume 2, Wiley-Interscience Publishers (1992), pp. 729-737, incorporated herein by reference in its entirety.

Histamine-2 (H-2 or H2) receptor antagonist compounds (H-2 antagonists) may be used in the compositions of the present invention. As used herein, selective H-2 antagonists are compounds that block H-2 receptors, but do not have meaningful activity in blocking histamine-1 (H-1 or H1) receptors.

Suitable denture care active ingredients can also include those used to control or mask odor. Examples of these include any of the known cyclodextrins such as unsubstituted cyclodextrins containing from six to twelve glucose units, especially alpha-cyclodextrin, beta-cyclodextrin, gamma-cyclodextrin, and/or their derivatives and/or mixtures thereof.

Suitable denture care active ingredients can also include those used in denture cleansers. These include the ingredients used to make commercial denture cleanser tablets such as Fixodent, Polident, and/or Efferdent denture cleanser tablets. Examples of suitable denture cleanser compositions are disclosed in U.S. Pat. Nos. 5,759,523, 5,827,505, 5,856,282, 6,004,538, 6,123,950, and 6,129,906, all of which are incorporated by reference herein.

Flavors, Sweeteners, Sensates, Fragrances, and Pigments

The water insoluble carriers of the present invention can be used to give improved delivery of sensates, flavors, and sweeteners to the oral cavity. Without being bound by theory, it is also believed that the hydrophobic nature of some of these water insoluble carriers can also inhibit stains, plaque, erosion, etc. Furthermore, the specific combinations and/or ratios of sensates, flavors, and/or sweeteners delivered via water insoluble carriers provide a high level of aesthetics and/or organoleptic benefits such as fresh feeling, clean feeling, slick teeth, smooth teeth, fresh breath, and/or, a pleasant taste. The compositions of the present invention with the components present in the specific ratios disclosed herein are believed to offer superior aesthetics and/or organoleptic benefits than those compositions that do not contain the components disclosed herein or are present in different ratios.

The ratios are defined as follows: The term "R1" as used herein refers to the ratio "weight of sensates/weight of flavors" in the composition. The term "R2" as used herein refers to the ratio "weight of flavors/weight of sweeteners" in the composition. The term "R3" as used herein refers to the ratio "weight of sensates/weight of sweeteners" in the composition. The term "R4" as used herein refers to the ratio "(weight of sensates+weight of flavors)/weight of Sweeteners)" in the composition.

In one embodiment, R1 is from about 0.0 to about 4.0, R2 is from about 0.0 to about 20, and R3 is from about 0.0 to about 20. In another embodiment, R1 is from about 0.5 to about 2.0, R2 is from about 1.0 to about 4.0, and R3 is from about 1.0 to about 4.0. In varying embodiment, R4 is from about 0.4 to about 40 or from about 2.0 to about 8.0. In one embodiment, it has been found that a composition with 4% Menthol (sensate), 4% Peppermint Oil (flavor), and 2% Saccharin (sweetener) (with R1 about 1.0, R2 about 2.0, R3 about 2.0, and R4 about 4.0) delivered in a petrolatum base provides a high level of aesthetics and/or organoleptic benefits.

The flavors for the present invention can be chosen from synthetic flavoring liquid and/or oils derived from plants leaves, flowers, fruits and so forth, and combinations thereof. Representative flavoring liquids include: vanillin, sage, marjoram, parsley oil, spearmint oil, cinnamon oil, oil of wintergreen (methylsalicylate), peppermint oils, clove oil, bay oil, anise oil, and eucalyptus oil. Also useful are artificial, natural or synthetic fruit flavors such as citrus oil including lemon, orange, banana, grape, lime, apricot and grapefruit and fruit essences including apple, strawberry, cherry, orange, pineapple and so forth; bean and nut derived flavors such as coffee, cocoa, cola, peanut, almond and so forth. Additionally, flavor adsorbed onto a hydrophilic matrix may be included, e.g. "spray-dried" flavors. Furthermore, encapsulated flavors may be included. In general, any denture care active may be spray-dried, encapsulated, and/or at least partially contained in a hydrophilic matrix. The amount of flavor employed is normally a matter of preference subject to such factors as flavor type and strength of flavor desired. In one embodiment, flavors may be present in amounts up to about 4%, in one embodiment about 0.05% to about 3.0%, in another embodiment about 0.8% to about 2.5%, by weight of the total composition.

Suitable sweeteners for the present invention include natural and artificial, water soluble, water insoluble and intense sweeteners. The sweetening agent may comprise sucralose, Rebiana, Acesulfame K, mono ammoniated glycyrrhizinate, dextrose, sucrose, maltose, dextrin, dried invert sugar, mannose, xylose, ribose, glucose, fructose, levulose, galactose, corn syrup, high fructose corn syrup, corn syrup solids, partially hydrolyzed starch, aspartame, saccharin, sugar alcohols such as sorbitol, mannitol, xylitol, maltitol, isomalt, and hydrogenated starch hydrolysate or combinations thereof. Sweeteners such as dipeptide based intense sweeteners, monellin, thaumaoccous danielli, and L-aspartyl L-phenylalanine methyl ester and soluble saccharin salts may be incorporated as sweeteners. The amount of the sweetener will vary with the type of sweetener selected and the desired level of sweetness. Sweetening agents and flavoring agents are typically used in denture care compositions at levels of from about 0.005% to about 5%, by weight of the total composition.

Suitable components for sensate benefit (warming or cooling agents) and/or fragrance include menthol, menthyl lactate, wintergreen oil, peppermint oil, spearmint oil, leaf alcohol, camphor, clove bud oil, eucalyptus oil, anethole, methyl salicylate, eucalyptol, cassia, 1-8 menthyl acetate, eugenol, oxanone, alpha-irisone, propenyl guaethol, cinnamon, thymol, linalool, benzaldehyde, cinnamaldehyde glycerol acetal known as CGA, and mixtures thereof, as well as coolants. The coolant can be any of a wide variety of materials. Included among such materials are carboxamides, menthol, ketals, diols, and mixtures thereof. Preferred coolants in the present compositions are the paramenthan carboxyamide agents such as N-ethyl-p-menthan-3-carboxamide, known commercially as "WS-3", N,2,3-trimethyl-2-isopropylbutanamide, known as "WS-23," and mixtures thereof. Additional preferred coolants are selected from the group consisting of menthol, 3-1-menthoxypropane-1,2-diol known as TK-10, manufactured by Takasago, menthone glycerol acetal known as MGA manufactured by Haarmann and Reimer, and menthyl lactate known as Frescolat® manufactured by Haarmann and Reimer. The terms menthol and menthyl as used herein include dextro- and levorotatory isomers of these compounds and racemic mixtures thereof. TK-10 is described in U.S. Pat. No. 4,459,425, Amano et al. WS-3 and other agents are described in U.S. Pat. No. 4,136,163, Watson, et al. The disclosures of both are herein incorporated by reference.

Another preferred coolant is the G-180 coolant, which is chemically N-(4-cyanomethylphenyl)-p-menthanecarboxamide, supplied by Givaudan as a 7.5% solution in flavor oil such as spearmint or peppermint. Addition of calcium ions may elevate the cooling effect of a 75 ppm G-180 formula to that of a 150 ppm G-180 formula, which would enable formulating products with lower levels of coolant. These agents may be present at a level of from about 0% to about 40%, in another embodiment from about 0.05 to about 5%, and in another embodiment from about 0.1 to about 2%, by weight of the composition.

Pigments may be added to the compositions herein to more precisely indicate the locations at which the composition has actually been in contact. Additionally, these substances may be suitable for modifying the color of the denture to satisfy the consumer. These substances comprise particles that when applied on the tooth surface modify that surface in terms of absorption and/or reflection of light. Such particles provide an appearance benefit when a film containing such particles is applied over the surfaces of the denture. Pigments, dyes, colorants, and lakes may also be added to modify the appearance of the compositions herein to render the product more acceptable to the consumer. Appropriate pigment levels are selected for the particular impact that is desirable to the consumer. For example, for dentures that are particularly dark or stained one would typically use pigments in sufficient amounts to lighten the teeth. On the other hand, where individual teeth or spots on the teeth are lighter than other teeth, pigments to darken the denture may be useful. In one embodiment, the levels of pigments and colorants may be in the range of about 0.001% to about 20%, in one embodiment from about 0.01% to about 15%, and in another embodiment from about 0.1% to about 10%, by total weight of the composition. In one embodiment the pigments and colorants are those selected from the group consisting of titanium dioxide, bismuth oxychloride, zinc oxide, Opatint D&C Red 27, CI 16185:1 Acid 27 Lake E123, CI 14720:1 Carmosoisine Aluminum Lake E122, Red 7 Lake, Red 30 Lake, and mixtures thereof.

The present invention may further comprise a viscosity modifier that inhibits settling and separation of components or controls settling in a manner that facilitates re-dispersion and may control flow properties. Suitable viscosity modifiers herein include mineral oil, organo-modified clays, petrolatum, silicas, and mixtures thereof. In one embodiment the viscosity modifier is silica. Where incorporated, the viscosity modifier can be present in the composition of the present invention at a level of from about 0.001% to about 99%, in one embodiment from about 0.01% to about 50%, and in another embodiment from about 0.1% to about 25% of the composition.

Additional denture care actives suitable for use in the present invention may include, but are not limited to, insulin, steroids, herbal and other plant derived remedies, and anti-neoplastics. Additionally, anti-gingivitis or gum care agents known in the art may also be included. Components, other than polybutene, which impart a clean feel to the teeth may optionally be included. These components may include, for example, baking soda or Glass-H. Also, it is recognized that in certain forms of therapy, combinations of these above-named agents may be useful in order to obtain an optimal effect. Thus, for example, an anti-microbial and an anti-inflammatory agent may be combined in a single chewing gum or confection piece to provide combined effectiveness.

In some embodiments, the water insoluble carrier itself may be the denture care active. In some embodiments, the water insoluble carrier may be the only denture care active, and in other embodiments, it may be combined with one or more other denture care actives.

Water Insoluble Carriers and Viscosity Index Improvers

The present composition comprises a water insoluble carrier. The water insoluble carrier offers the benefit of adhering well to the denture and not easily eroded, allowing extended time for it to deliver actives to the oral cavity. It has now further been discovered that a viscosity index improver can increase the beneficial effects of the water insoluble component and has additional benefits standing on its own. Historically, viscosity index improver was a term associated with the lubricant industry. The viscosity of a lubricant is closely related to its ability to reduce friction. The most desirable lubricant is one which will allow the easiest movement of two surfaces while still forcing the two moving surfaces apart, because this results in the lowest friction. However, as the viscosity of liquids tends to decrease as the temperature increases, many lubricants which work at lower temperatures are not thick enough to work at higher temperatures and those that are thick enough at the higher temperatures have a tendency to be too thick to work at the lower temperatures. The best lubricants will not vary much in viscosity over a desired temperature range and therefore will perform well throughout.

In order to better predict the range of temperatures at which a lubricant would work, the Society of Automotive Engineers established the Viscosity Index. The Viscosity Index highlights how a lubricant's viscosity changes with variations in temperature. The Viscosity Index shows the viscosity of materials at an arbitrary "low" temperature of 100° Fahrenheit (40° C.) and an arbitrary "high" temperature of 210° F. (100° C.).

After understanding the properties of lubricants over the set temperature ranges, it was discovered that adding certain types of compounds to the lubricants would make the viscosity of the lubricants more consistent through a broader temperature range. Thus, there was less of a decrease in the viscosity of the lubricant at the higher temperatures. Having a higher viscosity at the higher temperature allowed the lubricants to work better at the higher temperatures. The materials added to increase the viscosity at higher temperatures were defined as viscosity index improvers.

It has surprisingly been discovered that application of that principal also has relevance to denture care compositions. In general, denture care compositions can be made up of a myriad of materials based on the end use. For those which are intended to deliver an active to the oral cavity, they comprise a water insoluble carrier and a denture care active. During use, these compositions can get eroded and lose efficacy. The viscosity of the water insoluble carrier contributes to the speed at which the composition is eroded. Temperature-resistance of the viscosity imparted by the viscosity index improver results in resistance to erosion, which in turn results in the composition and actives being retained over time. This leads to extended and improved performance of the denture care compositions.

The temperature range most relevant for denture care compositions is from room temperature (25° C.) which deals with the viscosity of the denture care composition in the dispenser (tube or package, for example) to 40° C. which deals with the viscosity of the denture care composition in the mouth. While the temperatures in the mouth can reach upward of 60° C. when drinking a hot beverage, looking at the behavior of the compositions at 40° C. tends to be a good predictor of having increased beneficial properties at 60° C. as well. Thus, viscosity index improvers relevant for denture care compositions will make the viscosity more stable over the range of functional temperatures (i.e. 25° C. to 60° C.).

Thus, the use of viscosity index improvers alone or in combination with a water insoluble component will improve the erosion characteristics of this denture care composition and/or compatibility with denture care actives and thus provide an improved performance. Viscosity index improvers make the viscosity of the denture care composition more stable over the range of functional temperatures (i.e. about 25° C. to about 60° C.).

Aside from understanding the general principal of viscosity index improvers, another way to determine whether a material would work as a viscosity index improver in a denture care composition is to look at the instant viscosity ratio. The instant viscosity ratio measures the ratio of the viscosities of the prototype sample at room temperature (25° C.) and at an elevated temperature (40° C.). Compositions with a viscosity index improver tend to maintain their viscosity better at elevated temperatures than those compositions without a viscosity index improver. This is important because the denture care composition is placed into the mouth of a user which has a temperature generally higher than that of room temperature. Additionally, the temperature of a user's mouth can also be increased when ingesting hot beverages. The ability to maintain a higher viscosity at these higher temperatures contributes to less loss of the denture care composition during use.

The instant viscosity ratio can be measured as outlined below. In one embodiment, the instant viscosity ratio is greater than about 0.03. In another embodiment, the instant viscosity ratio is from about 0.03 to about 1.0. In additional embodiments, the instant viscosity ratio is from about 0.03, 0.04, 0.05, 0.06, 0.07, 0.08, 0.09, 0.10, 0.15, 0.20, 0.40 to about 0.05, 0.06, 0.07, 0.08, 0.09, 0.10, 0.15, 0.20, 0.40, 0.80, 1.00, or any combination thereof. In a further embodiment, the instant viscosity ratio is from about 0.03 to about 0.40. In other embodiments, the instant viscosity ratio is from about 0.04 to about 0.30 or from about 0.05 to about 0.20.

The following describes two samples, a reference sample (RS) and a prototype sample (PS). The reference sample is considered the standard and is made using the standard water insoluble components, which would not include a viscosity index improver, while the prototype sample is made using a viscosity index improver. A general formula is given for a RS and a PS, then formulas of a specific RS and a specific PS are given, along with their instant viscosity ratios for comparison.

Procedure to Prepare a Reference Sample (RS) and a Prototype Sample (PS)
Materials
To prepare a sample of the RS using standard WIC:
White Petrolatum ("Snow" from Penreco) 90%+Flavors (optional) 10%
To prepare a sample of the PS using the prototype viscosity index improver and WIC:
White Petrolatum ("Snow" from Penreco) 80%+Prototype Viscosity Index
Improver 10%+Flavors (optional) 10%
Procedure The Reference Sample is prepared using the following procedure:

Melt the petrolatum in an oven. Melt and make a premix of the flavors in a separate container. Add the flavor premix to the molten petrolatum. Thoroughly mix using a speed-mixer. Fill the sample into a suitable container, such as a foil tube. Allow samples to equilibrate for at least one day at room temperature.

The Prototype sample is prepared using the following procedure:

Melt and mix the petrolatum and prototype viscosity index improver in an oven. Melt and make a premix of the flavors in a separate container. Add the flavor premix to the molten mixture of petrolatum and prototype viscosity index improver. Thoroughly mix using a speed-mixer. Fill the sample into a suitable container, such as a foil tube. Allow samples to equilibrate for at least one day at room temperature.

Whenever possible, the RS and PS are made with the same manufacturing procedure and same optional ingredients. This is done to provide a standard matrix to test the differences between a variety of viscosity index improvers by keeping all other variables the same.

If it is necessary to accommodate any property of the prototype viscosity index improver or viscosity index improver/water insoluble component combination that is not accommodated by the process detailed above, the processing temperature profile can be modified as needed. Additionally, if the above testing formulation gives a PS which is too thick to test for the instant viscosity ratio as described below, then the sample may need to be diluted with additional water insoluble component like mineral oil.

The above process tests for viscosity index improvers at a level of about 10%. It is believed that testing the prototype viscosity index improvers at 10% will help set-up a baseline, meaning that a finding of viscosity index improver properties at a level of 10% is indicative of viscosity index improver properties at high levels. That being said, a prototype viscosity index improver which is tested at 10% and is found not to have viscosity index improver properties at that level may have them at a higher percentage and should be tested at a higher level to confirm.

The above process can also be scaled up and used for general manufacturing at the temperature appropriate for the viscosity index improver and/or water insoluble component of the denture adhesive article.

The following table, Table 1, includes formulas for a particular reference sample (RS) and a particular prototype sample (PS). These are disclosed to illustrate the difference in instant viscosity ratio when a viscosity index improver is used, in this case, microcrystalline wax.

TABLE I

|  | A<br>RS<br>% | B<br>PS<br>% |
|---|---|---|
| Mixed Mint Oils | 4 | 4 |
| Menthol | 4 | 4 |
| Saccharin Powder | 2 | 2 |
| Petrolatum | 90 | 80 |
| Microcrystalline Wax W-835<br>(by Witco Crompton, Sonneborn) | 0.00 | 10 |

The instant viscosity of the PS at 25° C. is 207 Ps and at 40° C. is 20 Ps. This gives an instant viscosity ratio for the PS of 0.10. In contrast to this, the RS has an instant viscosity at 25° C. of 98 Ps and at 40° C. of 2.0 Ps. This gives an instant viscosity ratio for RS of 0.02. The higher instant viscosity ratio of PS shows that it is more temperature resistant than the reference water insoluble component and thus, microcrystalline wax will work as a viscosity index improver in that denture care composition.

Some examples of viscosity index improvers include polymethacrylates, olefin copolymers, hydrogenated styrene-diene copolymers, styrene polyesters, rubber, polyvinylchloride, nylon, fluorocarbon, polyurethane prepolymer, polyethylene, polystyrene, polypropylene, cellulosic resins, acrylic resins, microcrystalline wax, elastomers, poly(n-butyl vinyl ether), poly(styrene-co-maleic anhydride), poly(alkyl fumarate co-vinyl acetate), alkylated polystyrene, poly(t-butyl styrene), or combinations thereof.

Examples of polymethacrylates include, for example, polyacrylate-co-methacrylate, polymethacrylate-co-styrene, or combinations thereof. Examples of elastomers include, for example, hydrogenated styrene-co-butadiene, hydrogenated styrene-co-isoprene, ethylene-ethylene-propylene polymer, ethylene-propylene polymer, styrene-ethylene-ethylene-propylene-styrene polymer or combinations thereof. An example of a rubber includes hydrogenated polyisoprene. Other examples of viscosity index improvers can be found in "Chemistry and Technology of Lubricants," Chapman and Hall ($2^{nd}$ Ed. 1997).

In one embodiment, the viscosity index improver is selected from the group consisting of polymethacrylates, olefin copolymers, hydrogenated styrene-diene copolymers, styrene polyesters, and combinations thereof. In another embodiment, the viscosity index improver is selected from the group consisting of rubber, polyvinylchloride, nylon, fluorocarbon, polyurethane prepolymer, polyethylene, polystyrene, polypropylene, cellulosic resins, acrylic resins, microcrystalline wax, elastomers, and combinations thereof. In an additional embodiment, the viscosity index improver comprises microcrystalline wax, polyethylene, rubber, elastomers, or a combination thereof.

In another embodiment, the viscosity index improver is polyethylene, such as A-C 1702 and A-C 6702 made by Honeywell. In another embodiment, the viscosity index improver is substantially free of amorphous polyethylene having a molecular weight of at least about 80,000. In an additional embodiment, when the viscosity index improver consists of a polyethylene having an average molecular weight of from about 1000 to about 21,000 then the component is substantially free of a mixed partial salt of a lower AVE/MA salt of calcium and alkali cations selected from the group consisting of sodium, potassium, and quaternary ammonium cations.

In another embodiment, the viscosity index improver comprises microcrystalline wax. In one embodiment, the microcrystalline wax is refined and/or substantially pure. In an additional embodiment, petrolatum does not contribute the microcrystalline wax. In one particular embodiment, the microcrystalline wax has a melting point ranging from about 75° C. to about 85° C. In another embodiment the microcrystalline wax is manufactured by Crompton, Sonneborn (Witco) and referred to and sold under the trademark Mutiwax®W-835.

In some embodiments, viscosity index improvers are used in an amount from about 0.001% to about 90.0%. In varying embodiments, the viscosity index improvers are present in an amount from about 1%, 2, 5, 10, 15, 20, 30, 40 to about 10, 15, 20, 30, 40, 50, 60, 70, 80, 90%, or any combination thereof. In one embodiment, the viscosity index improver is from about 40% to about 60%, when the denture care composition is preformed. In one embodiment, the viscosity index improver is from about 1.0% to about 15.0% when the denture care composition can be dispensed from a tube. In one embodiment, the viscosity index improver is water insoluble and/or non-swellable in water.

Suitable water insoluble carriers are described in U.S. Published Patent Application 2007/0185233, the substance of which is incorporated herein. In one embodiment the water insoluble component is at a level from about 2, 5, 10, 20, 25, 30, 35% to about 45, 50, 60, 70, 90%, and/or any combination thereof to create ranges, by weight of the composition. In another embodiment the water insoluble component level is from about 20% to about 70%, from about 25% to about 60%, or from about 35% to about 60% by weight of the composition. In yet another embodiment the water insoluble component is both water insoluble and substantially non-swellable in water. The water insoluble carrier may be a combination of two or more water insoluble carriers.

In one embodiment the water insoluble component is a water insoluble liquid component selected from the group consisting of mineral oil, natural and synthetic oils, fats, silicone, silicone derivatives, dimethicone, silicone resins, hydrocarbons, hydrocarbon derivatives, essential oils, vegetable oils, polybutenes, caprylic/capric triglycerides, corn, soy bean, cottonseed, castor, palm oil, coconut oils, animal oils, fish oil, oleic acid, and mixtures thereof. In another embodiment the water insoluble component is a PDMS gum, or a mixture of PDMS gum with an MQ resin cast from a solvent such as volatile isoparrafin (see U.S. Pat. No. 6,074,654).

In one embodiment the water insoluble component is a water insoluble thermoplastic component that is selected from the group consisting of rubber, elastomers, plastomers, natural wax, synthetic wax, polyvinyl chloride, nylon, fluorocarbon, polyurethane prepolymer, polyethylene, polystyrene, polypropylene, cellulosic resins, acrylic resins, petrolatum, and mixtures thereof. In another embodiment the water insoluble thermoplastic component is selected from the group consisting of natural wax, synthetic wax, petrolatum, polyethylene, and mixtures thereof. In yet another embodiment the water insoluble thermoplastic component is selected from the group consisting of polyethylene, petrolatum, paraffin wax, microcrystalline wax, polypropylene, polystyrene, and mixtures thereof; in another embodiment it is selected from the group consisting of polyethylene, microcrystalline wax, and mixtures thereof. In one embodiment, the water insoluble component is petrolatum.

In one embodiment the water insoluble thermoplastic component comprises elastomers such as Ethylene-Ethylene-Propylene rubber, Ethylene-Propylene rubber, Styrene-Ethylene-Ethylene-Propylene-Styrene rubber, and combinations thereof, and these may optionally be further combined with waxes.

In one embodiment the water insoluble thermoplastic component is a natural or synthetic wax. These waxes include natural waxes such as animal, vegetable, and mineral wax. Animal waxes include beeswax, lanolin, shellac wax, Chinese wax, etc. Vegetable waxes include carnauba, candelilla, bayberry, sugar cane, etc., and mineral waxes include fossil and earth waxes (ozocerite, ceresin, montan), and petroleum waxes such as paraffin, microcrystalline, etc. In one embodiment the waxes herein are natural waxes selected from the group consisting of beeswax, candelilla, candela, carnauba, paraffin, microcrystalline wax, Fischer-Tropsch waxes, and mixtures thereof.

In another embodiment the wax is microcrystalline wax manufactured by Crompton, Sonneborn (Witco) and referred to and sold under the trademark Mutiwax W-835. This wax has a melt point ranging from about 73.9° C. to about 79.4° C. (ASTM D127), a penetration at 25° of from about 60 to about 80 (ASTM D1321), a kinematic viscosity at 98.9° C. of from about 75 to about 90 (ASTM D2161), a flash point, COC, of about 246° C. min. (ASTM D92), and a congealing point of about 77° C. (ASTM D938).

In another embodiment the water insoluble thermoplastic component is polyethylene, such as A-C 1702 and A-C 6702 made by Honeywell, with a penetration value of 98.5 and 90.0, respectively, under ASTM D1321. In one embodiment, if the composition contains polyethylene oxide, then either the water insoluble component is thermoplastic or the composition may not include a fibrous paper web or paper laminate.

In one embodiment, the composition herein is substantially free of honey mixed with alcohol. In another embodiment the composition is substantially free of polyvinyl acetate resin in ethyl alcohol. In one embodiment, the water insoluble carrier is hydrophobic. In one embodiment, the composition comprises a uniform mixture of one or more denture care actives and one or more water insoluble carriers.

Article

In some embodiments, the present invention may be an article, shaped and designed to fit, and conform to contoured surfaces such as a denture.

In one embodiment, the term "dry tack" as used herein means that the articles exhibit minimal and/or no adhesive or cling properties in the dry state until activated by pressure applied by a user. In one embodiment, the article has a shear storage modulus G' (measured in dynes/cm² at a frequency of about 1 Hz at about 25 C) from about $1\times10^6$, $3\times10^6$, $5\times10^6$, $1\times10^7$, $5\times10^7$, and $8\times10^7$ to about $5\times10^8$, $5\times10^7$, $1\times10^8$, $5\times10^9$, $1\times10^9$, and $1\times10^{10}$ and/or any combination thereof.

Miscellaneous Optional Ingredients

Plasticizing Agent

The denture care compositions of the present invention may also optionally comprise a safe and effective amount of one or more toxicologically-acceptable plasticizers. In one embodiment, the level of the plasticizing agent ranges from about 0.0% to about 40%, in one embodiment from about 0.01% to about 40%, in another embodiment from about 1% to about 10%, in another embodiment from about 2% to about 5%, by weight of the composition. In yet another embodiment the denture care composition does not comprise a plasticizer. In another embodiment the plasticizer is water insoluble.

In one embodiment, the denture care composition, when extruded thermoplastically, does not cure and set as a result of the action of the plasticizer component. In another embodiment the plasticizer component does not solidify the water insoluble component or the denture care composition. In another embodiment the water insoluble thermoplastic component does not cure and set.

Alternatively, in one embodiment the denture care composition may be substantially free of plasticizers. In one embodiment the denture care composition may be substantially free of polyethylmethacrylate, triacetin, phthalic acid derivative, glycerol triacetate, citric acid derivative, phosphoric acid derivative, glycol, glycol derivative, paraffin wax, a pentaerythritol ester of a fatty acid, stearic acid derivative, glycerol monostearate, polyethylene glycol, butyl phthalyl butyl glycolate, butyl phthalyl butyl glycolate, dimethyl phthalate, dibutyl phthalate, triacetin, triethyl citrate, acetyl triethyl citrate, acetyl tributyl citrate, triphenyl phosphate, diethylene glycol, caprylic triglyceride, capric triglyceride, propylene glycol dicaprylate/caprate and/or combinations thereof.

Substantivity Agent

In addition to those components listed above, the denture care composition may additionally include other components. One example of these additional components includes substantivity agents. One group of substantivity agents is organophosphates. Suitable organophosphate compounds have a strong affinity for the tooth surface and have sufficient surface binding propensity to desorb pellicle proteins and remain affixed thereon. The phosphate groups of the organophosphate attach themselves to cations, in particular calcium ions in teeth or some other positively charged sites such as protein residues on the mucosal surface and thus serve to anchor the hydrophobic portion of the molecule onto the surface thereby modifying it to be hydrophobic. The phosphate groups provide ready bonding/binding to cationic and charged surfaces via electrostatic interaction, hydrogen bonding, or complexation, which leads to ready deposition of the organophosphate upon application to form a coating on the treated surface. The strong bond results in longer retention or durability and substantivity of the coating.

Examples of suitable organophosphate compounds are mono-, di- or triesters represented by the following general structure wherein $Z^1$, $Z^2$, or $Z^3$ may be identical or different, at least one being an organic moiety, preferably selected from linear or branched, alkyl or alkenyl group of from 6 to 22 carbon atoms, optionally substituted by one or more phosphate groups; alkoxylated alkyl group or alkoxylated alkenyl group.

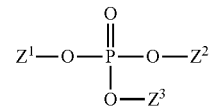

Some preferred agents include alkoxylated alkyl or alkenyl phosphate esters represented by the following structure:

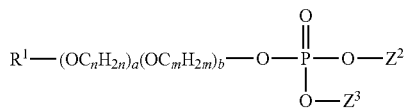

wherein $R^1$ represents a linear or branched, alkyl or alkenyl group of from 6 to 22 carbon atoms, optionally substituted by one or more phosphate groups; n and m, are individually and separately, 2 to 4, and a and b, individually and separately, are 0 to 20; $Z^2$ and $Z^3$ may be identical or different, each represents hydrogen, alkali metal, ammonium, protonated alkyl amine or protonated functional alkyl amine such as an alkanolamine, or a $R^1$—$(OC_nH_{2n})_a(OC_mH_{2m})_b$—group. Preferably, $R^1$ is an alkyl group of at least 10 carbon atoms and a and b are each no more than 10 in order to maintain overall hydrophobic character of the organophosphate and the degree of hydrophobicity imparted to the surface.

In one embodiment, the substantivity agent includes mono- di- and tri-alkyl and alkyl (poly)alkoxy phosphates such as dodecyl phosphate, lauryl phosphate; laureth-1 phosphate; laureth-3 phosphate; laureth-9 phosphate; dilaureth-10 phosphate; trilaureth-4 phosphate; $C_{12-18}$ PEG-9 phosphate and salts thereof. Many are commercially available from suppliers including Croda; Rhodia; Nikkol Chemical; Sunjin; Alzo; Huntsman Chemical; Clariant and Cognis. In one embodiment, the substantivity agent comprises monoalkyl phosphate.

Active

Another example of an additional component includes actives. Some examples of actives include various fluoride salts for caries prevention and remineralization; gingivitis prevention by the use of antimicrobial agents such as triclosan, cetylpyridinium chloride, stannous fluoride, zinc citrate or essential oils; and hypersensitivity control through the use of ingredients such as strontium chloride, stannous fluoride, or potassium nitrate; pyrophosphate salts can be used as antitartar agents; peroxides can be used for bleaching and antiseptics; and polymeric mineral surface active agents such as phosphorylated polymers, in particular polyphosphates that bind to teeth, or metal ions such as stannous, zinc or copper that form insoluble compounds that deposit onto teeth, can be used for erosion protection or sensitivity protection. These actives can be used alone or in combination.

Adhesive Component

Another example of an additional component includes adhesive components. The present invention may optionally further comprise a safe and effective amount of an adhesive component, generally at a low level just enough to help the composition to adhere to the wet mucosal tissue, but not enough to significantly improve the retention of the denture.

In general, adhesive components are hydrophilic particles that become sticky when activated by moisture or are hydrophilic liquids. In varying embodiments, the adhesive components herein are mucoadhesive, adhesive to the teeth, hydrophilic, water soluble, have the property of swelling upon exposure to moisture, or any combination thereof.

In one embodiment, the adhesive component is selected from the group consisting of: cellulose, cellulose derivatives (such as methylcellulose, carboxymethylcellulose, hydroxyethylcellulose, hydroxypropylcellulose, hydroxy-propylmethylcellulose, corn starch, and mixtures thereof), starch, starch derivatives, saccharide, saccharide derivatives, polyethylene oxides, polyethylene glycols, polyvinyl alcohols, carrageenan, alginates, karaya gums, xanthan gums, guar gums, gelatins, algins, tragacanth, chitosan, acrylamide polymers, carboxypolymethylenes, polyamines, poly quaternary compounds, polyvinylpyrrolidone, AVE/MA, salts of AVE/MA, mixed salts of AVE/MA, polymeric acids, polymeric salts, polyhydroxy compounds, and mixtures thereof.

Gellant Agents

The compositions of the present invention may also optionally comprise a safe and effective amount of one or more toxicologically-acceptable gellants. In one embodiment, the level of the gellant agent ranges from about 0.01% to about 40%, in another embodiment from about 1% to about 10%, in another embodiment from about 2% to about 5%, by weight of the composition.

Other Optional Ingredients

Other suitable ingredients include colorants, preservatives (such as methyl and propyl parabens), thickeners such as silicon dioxide, and polyethylene glycol. Colorants, preservatives, thickeners may be present at levels of from about 0% to about 20%, by weight of the composition, in another embodiment from about 0.1% to about 10%, by weight.

Additionally, the compositions may also comprise one or more solvents. These optional solvents may be miscible with the water insoluble component and/or be capable of being dissipated in-situ. In one embodiment, these solvents may be dissipated in-situ by evaporation, dissolution, dispersion, bioabsorption, or any other suitable means. In another embodiment these solvents may be dissipated in-situ to leave behind a denture care composition. Such solvents may include materials with a viscosity ranging from 0.01, 0.1, 1, 5 centipoise at 20° C., to 5, 10, 100, 1000 centipoise at 20° C., in any combination of these levels. In one embodiment, these solvents may be silicones, hydrocarbons, iso-dodecane, iso-hexadecane, iso-eicosane, and/or polyisobutene. Suitable grades of solvents include the Permethyl series (sold by Prespers Inc., New Jersey) such as Permethyl 97A, 99A, 101A, 102A, and mixtures thereof.

Method of Preparation

The denture care composition is suitably made as follows: Combine the water insoluble carrier and any denture care active ingredients into a mixing vessel and mix well with any means known within the art, for example, with a spatula or mixer. Heat the composition, if needed, to facilitate mixing. Continue mixing the composition until homogenous. Where a denture care active is included in solid particulate form, the addition of a viscosity modifier, such as silica, may be appropriate to keep the particulate dispersed and suspended within the composition.

If the composition to be made is an article, the following processes can be used. The articles utilized in accordance with the invention are formed by processes conventional in the arts, e.g. the film-making industries such as casting, coating, calendaring, extrusion. In one embodiment, the separate components of the article are melted and then blended in a mixing tank until a homogeneous mixture is achieved. Thereafter, the melted mixture may be cast to an acceptable thickness, on an appropriate substrate. Examples of such substrates include Mylar, continuous moving stainless steel belt (which may eventually enter a dryer section if needed), release paper, and the like. The articles are then cooled. The articles may then be dried if needed, e.g. in a forced-air oven. The article may then be cut into desired shapes with desired dimensions and then stacked and/or subsequently packaged.

In one embodiment, after processing, the article is then die-cut into desired shapes. These shapes may facilitate application of the article to the dentures.

Another conventional film-making process known in the art is extrusion. This method is possible with films wherein the film-forming ingredient comprises a variety of extrudable materials. The mechanical particulars of the extrusion process, e.g. the particular equipment utilized, the extruding force, the shape and temperature of the orifice and/or dies are considered to be within the skill of the art and can be varied in a known manner to achieve the physical characteristics of the articles described herein.

In one embodiment, the thickness of the denture care composition that is an article is generally from about 0.1 mm to about 2.5 mm, in another embodiment from about 0.4 mm to about 1.5 mm, in another embodiment from about 0.5 mm to about 1 mm. The article may be thicker or thinner depending on the degree of cushioning desired by the user or wearer.

In one embodiment, the denture care composition that is an article may optionally be multiphase or have visually distinct phases. In another embodiment the articles herein may optionally have a release liner.

Method of Use

In using the present denture care composition, the user removes the denture from the oral cavity and applies the denture care composition disclosed herein directly to the surface of the denture. The composition may be applied using a brush, pen applicator, dropper, doe's foot applicator or other application device. The composition may also be applied by manually placing it on the denture, by finger, cotton swab, or dental stick or the like or by dipping the denture into the denture care composition. In some embodiments, after the denture care composition is applied to the surface of a denture, the denture may then be applied to the oral cavity. In some embodiments, the denture care active may be a denture cleanser, in which case, after the denture care composition is applied to the surface of the denture, the denture may be immersed in water.

It is not necessary to prepare the denture before applying the composition of the present invention. For example, the user may or may not choose to brush or cleanse the denture before applying the composition. The surfaces of the denture are neither required to be dried nor to be excessively wet with saliva or water prior to application. However, it is believed that adhesion to the denture surfaces will be improved if the surfaces are drier when the composition is applied.

EXAMPLES

The following non-limiting examples further illustrate and describe the embodiments of the subject invention wherein both essential and optional ingredients are combined. It is to be understood that the examples are given solely for the purpose of illustration and are not to be construed as limiting the scope of the present invention, as many variations thereof are possible without departing from the spirit and scope of the invention.

Examples 1-7

| Ingredients | 1 % weight | 2 % weight | 3 % weight | 4 % weight | 5 % weight | 6 % weight | 7 % weight |
|---|---|---|---|---|---|---|---|
| Microcrystalline Wax 445 | 95.00 | 85.00 | 85.00 | 85.00 | 85.00 | 85.00 | 75.00 |
| Mixed Mint Flavor | 2.00 | 2.00 | 2.00 | 2.00 | 2.00 | 2.00 | 2.00 |
| Menthol | 2.00 | 2.00 | 2.00 | 2.00 | 2.00 | 2.00 | 2.00 |
| Carbamide Peroxide | — | — | — | 5.00 | — | — | — |
| CMC (7H3) | — | 5.00 | — | — | — | — | — |
| CMC (7LF) | — | — | — | — | 5.00 | — | 10.00 |
| Glass-H | — | — | 5.00 | — | — | — | — |
| Sodium Starch Glycolate | — | — | — | — | — | 5.00 | — |
| Saccharin | 1.00 | 1.00 | 1.00 | 1.00 | 1.00 | 1.00 | 1.00 |
| Microcrystalline Wax W835 | — | 5.00 | 5.00 | 5.00 | 5.00 | 5.00 | 10.00 |
|  | 100 | 100 | 100 | 100 | 100 | 100 | 100 |

The levels of each ingredient may be varied by 5, 20, 25, 50, 100% or more in the above examples. Furthermore, each of the above example formulations may also be mixed with each other to provide hybrid-examples.

Procedure for Making Examples 1-7:

1. Melt wax in oven set at 90° C.;
2. Shake-blend powder items in jar (taking care to break up lumps with spatula);
3. Add powder blend from step 2 into molten wax and wet it into wax with spatula;
4. Mix in speed mixer at 1000 rpm for two minutes; remove and scrape away material from walls and corners with spatula;
5. Mix in speed mixer for an additional two minutes two times; total mixing time equals six minutes;
6. Extrude into thin strips of about 0.7 mm thickness and die-cut into desired shapes and sizes.

Examples 8-13

| Ingredients | 8 % weight | 9 % weight | 10 % weight | 11 % weight | 12 % weight | 13 % weight |
|---|---|---|---|---|---|---|
| Mixed Mint Flavor | 2.00 | 2.00 | — | — | 4.00 | 2.00 |
| Menthol | 2.00 | 2.00 | — | — | 4.00 | 2.00 |
| Any Denture Care Active | — | 2.00 | 20.00 | 2.00 | — | 2.00 |
| Saccharin | 1.00 | 1.00 | — | — | 2.00 | 1.00 |
| Petrolatum* | 95.00 | 93.00 | 80.00 | 98.00 | 90.00 | 93.00 |
|  | 100 | 100 | 100 | 100 | 100 | 100 |

*Can also be any other water insoluble component such as silicones oils, polyethylene, or mixtures thereof.

The levels of each ingredient may be varied by 5, 20, 25, 50, 100% or more in the above examples. Furthermore, each of the above example formulations may also be mixed with each other to provide hybrid-examples.

Procedure for Making Examples 8-13:
1. Melt the petrolatum in oven at 70° C.;
2. Add other ingredients;
3. Mix until uniform;
4. Fill into tubes, or shape into strips as suitable.

Examples 14-21

| Ingredients | 14 % weight | 15 % weight | 16 % weight | 17 % weight | 18 % weight | 19 % weight | 20 % weight | 21 % weight |
|---|---|---|---|---|---|---|---|---|
| Mint Flavors | 2.00 | 2.00 | 2.00 | 2.00 | 2.00 | 2.00 | 2.00 | 4.00 |
| Menthol | 2.00 | 2.00 | 2.00 | 2.00 | 2.00 | 2.00 | 2.00 | 4.00 |
| Versagel 1600M | — | 95.00 | — | — | — | — | — | — |
| Versagel 500M | — | — | 95.00 | — | — | — | — | — |
| Saccharin | 1.00 | 1.00 | 1.00 | 1.00 | 1.00 | 1.00 | 1.00 | 2.00 |
| Citric Acid | — | — | — | — | 2.50 | 2.50 | — | — |
| Sodium Bicarbonate | — | — | — | — | 2.50 | — | — | — |
| Erythritol | — | — | — | — | — | — | 10.00 | — |
| Carbamide Peroxide | — | — | — | — | — | 5.00 | — | — |
| Penreco Ultima Petrolatum | — | — | — | 95.00 | — | — | — | — |
| Petrolatum | 95.00 | — | — | — | 90.00 | 87.50 | 85.00 | 90.00 |
|  | 100 | 100 | 100 | 100 | 100 | 100 | 100 | 100 |

The levels of each ingredient may be varied by 5, 20, 25, 50, 100% or more in the above examples. Furthermore, each of the above example formulations may also be mixed with each other to provide hybrid-examples.

Procedure for Making Examples 14-21:

1. Heat petrolatum/versagel in oven at 60° C.;
2. Add other ingredients and mix in speed mixer for two minutes at 1000 rpm. Repeat three times;
3. Fill into tubes.

The levels of each ingredient may be varied by 5, 20, 25, 50, 100% or more in the above examples. Furthermore, each of the above example formulations may also be mixed with each other to provide hybrid-examples.

Examples 22-31

| Ingredients | 22 % weight | 23 % weight | 24 % weight | 25 % weight | 26 % weight | 27 % weight | 28 % weight | 29 % weight | 30 % weight | 31 % weight |
|---|---|---|---|---|---|---|---|---|---|---|
| Peppermint | — | — | — | — | — | — | 3.00 | 3.00 | 3.00 | 3.00 |
| Microcrystalline Wax W835 | 78.00 | 68.00 | 68.00 | — | — | — | 63.00 | — | — | — |
| Carbamide Peroxide | 12.00 | 12.00 | 12.00 | 12.00 | 12.00 | 12.00 | 12.00 | 12.00 | 12.00 | — |
| Microcrystalline Wax W445 | — | — | — | 78.00 | 68.00 | 68.00 | — | 63.00 | 83.00 | 95.00 |
| Saccharin | — | — | — | — | — | — | 2.00 | 2.00 | 2.00 | 2.00 |
| Carboxymethyl cellulose | 10.00 | 20.00 | 20.00 | 10.00 | 20.00 | 20.00 | 20.00 | 20.00 | — | — |
| | 100 | 100 | 100 | 100 | 100 | 100 | 100 | 100 | 100 | 100 |

The levels of each ingredient may be varied by 5, 20, 25, 50, 100% or more in the above examples. Furthermore, each of the above example formulations may also be mixed with each other to provide hybrid-examples.

Procedure for Making Examples 22-31:
1. Melt wax in oven set at 90° C.;
2. Mortar and pestle powder items individually;
3. Shake-blend powder items (except peroxide) in separate jar, taking care to break up lumps with spatula;
4. Add peppermint into molten wax and mix with spatula;
5. Add powder blend from step 3 into molten wax and wet it into wax with spatula;
6. Mix in speed mixer at 1000 rpm for two minutes; remove and scrape away material from walls and corners with spatula;
7. Add carbamide peroxide and wet it into wax with spatula;
8. Mix in speed mixer for an additional 2 minutes two times; total mixing time equals six minutes;
9. Shape into strips and die-cut into suitable shapes and sizes.

Examples 32-34

| Ingredients | 32 % weight | 33 % weight | 34 % weight |
|---|---|---|---|
| Microcrystalline Wax W835 | 47 | 47 | 40 |
| Denture Cleanser Tablet* (Powdered) | 53 | 43 | 0 |
| Effervescent Powders | 0 | 0 | 53 |
| Carboxymethyl cellulose | 0 | 10 | 10 |
| | 100 | 100 | 100 |

*Can be any commercially available denture cleanser tablet including Fixodent, Polident and/or Efferdent.

Procedure for Making Examples 32-34:
1. Melt wax in oven set at 90° C.;
2. Crush or mill the cleanser tablet(s) into a powder;
3. Shake-blend powder items in separate jar, taking care to break up lumps with spatula;
4. Add powder blend from step 3 into molten wax and wet it into wax with spatula;
5. Mix in speed mixer at 1000 rpm for two minutes; remove and scrape away material from walls and corners with spatula;
6. Mix in speed mixer for an additional two minutes two times; total mixing time equals six minutes;
7. Shape into strips and die-cut into suitable shapes and sizes.

The levels of each ingredient may be varied by 5, 20, 25, 50, 100% or more in the above examples. Furthermore, each of the above example formulations may also be mixed with each other to provide hybrid-examples. Furthermore, each of the above example formulations may also be layered onto each other to provide hybrid-examples.

Strips from examples 32-34 can be molded onto the teeth portion of dentures and immersed into a cup of water. These compositions help clean the dentures while soaking in the water.

Examples 35A-K

|  | A % | B % | C % | D % | E % | F % | G % | H % | I % | J % | K % |
|---|---|---|---|---|---|---|---|---|---|---|---|
| Microcrystalline Wax W835 | 0 | 48 | 0 | 0 | 48 | 0 | 0 | 0 | 10 | 10 | 0 |
| Mineral Oil | 0 | 42 | 0 | 0 | 34 | 0 | 0 | 0 | 0 | 0 | 0 |
| Petrolatum | 90 | 0 | 0 | 82 | 0 | 90 | 89 | 88 | 80 | 79 | 94 |
| Mixed Mint Flavor | 4 | 4 | 4 | 8 | 8 | 8 | 2 | 4 | 4 | 4 | 4 |
| Menthol | 4 | 4 | 4 | 8 | 8 | 1 | 8 | 4 | 4 | 4 | 0 |
| Saccharin (Powder) | 2 | 2 | 2 | 2 | 2 | 1 | 1 | 4 | 2 | 2 | 2 |
| Versagel 750 M (or 1600 M) | 0 | 0 | 90 | 0 | 0 | 0 | 0 | 0 | 0 | 1 | 0 |
|  | 100.0 | 100.0 | 100.0 | 100.0 | 100.0 | 100.0 | 100.0 | 100.0 | 100.0 | 100.0 | 100.0 |
| R1 | 1.00 | 1.00 | 1.00 | 1.00 | 1.00 | 0.13 | 4.00 | 1.00 | 1.00 | 1.00 | 0.00 |
| R2 | 2.00 | 2.00 | 2.00 | 4.00 | 4.00 | 8.00 | 2.00 | 1.00 | 2.00 | 2.00 | 2.00 |
| R3 | 2.00 | 2.00 | 2.00 | 4.00 | 4.00 | 1.00 | 8.00 | 1.00 | 2.00 | 2.00 | 0.00 |
| R4 | 4.00 | 4.00 | 4.00 | 8.00 | 8.00 | 9.00 | 10.00 | 2.00 | 4.00 | 4.00 | 2.00 |

To make the above example compositions B, E, I, and J the wax is melted at 95° C. and the other components are mixed into it at the elevated temperature. To make the above examples A, C, D, F, G, H, and K the petrolatum and/or Versagel is heated to about 70° C. and the other components are mixed in at the elevated temperature. For all examples, the compositions are allowed to come to room temperature prior to use.

Furthermore, each of the above example formulations may also be mixed with each other to provide hybrid-examples.

Examples 35L-N

|  | L % | M % | N % |
|---|---|---|---|
| Petrolatum | 90 | 92 | 94 |
| Saccharin | 2 | 0 | 2 |
| Mint | 4 | 4 | 0 |
| Menthol | 4 | 4 | 4 |
|  | 100.0 | 100.0 | 100.0 |
| R1 | 1.00 | 1.00 | >100 |
| R2 | 2.00 | >100 | 0.00 |
| R3 | 2.00 | >100 | 2.00 |
| R4 | 4.00 | >100 | 2.00 |

To make the above examples L, M, and N, the petrolatum is heated to about 70° C. and the other components are mixed in at the elevated temperature. For all examples, the compositions are allowed to come to room temperature prior to use. After the samples are made, they are placed into a container. The consumer preference for taste is tested by allowing a consumer to dip a disposable lip gloss applicator into the container and tasting the sample. The consumer then picks the sample they prefer. The consumer also rates each sample on a scale of −4 to +4 (with −4 being "Dislike Extremely" and +4 being "Like Extremely"). Each of Samples M and N are directly compared with Sample L, so each consumer tests Sample L versus Sample M, then Sample L versus Sample N. The preferences and ratings for these comparisons are below.

|  | Sample L vs. Sample M | Sample L vs. Sample N |
|---|---|---|
| Rating | Sample L is preferred over Sample M by 100% of the Panelists<br>Sample L is rated: 2.4<br>Sample M is rated: −1.8 | Sample L is preferred over Sample N by 67% of the Panelists<br>Sample L is rated: 2.11<br>Sample N is rated: 0.67 |

The above results indicate Sample L is strongly preferred over and rated much higher than Sample M. Specifically, Sample L, with R1/R2/R3/R4 ratios of 1/2/2/4, is strongly preferred over and rated much higher than Sample M with R1/R2/R3/R4 ratios of 1/>100/>100/>100.

The above results also indicate that Sample L is preferred over and rated higher than Sample N. Specifically, Sample L, with R1/R2/R3/R4 ratios of 1/2/2/4, is preferred over and rated higher than Sample N with R1/R2/R3/R4 ratios of >100/0/2/2.

Examples 35O-R

|  | O % | P % | Q % | R % |
|---|---|---|---|---|
| Petrolatum | 91.8 | 98.5 | 91.8 | 90 |
| Saccharin | 0.16 | 0.3 | 0.16 | 2 |
| Mint | 4 | 0.6 | 4 | 4 |
| Menthol | 4 | 0.6 | 4 | 4 |
|  | 100.0 | 100.0 | 100.0 | 100.0 |
| R1 | 1.00 | 1.00 | 1.00 | 1.00 |
| R2 | 25.00 | 2.00 | 25.00 | 2.00 |
| R3 | 25.00 | 2.00 | 25.00 | 2.00 |
| R4 | 50.00 | 4.00 | 50.00 | 4.00 |

To make the above examples O, P, Q, and R, the petrolatum is heated to about 70° C. and the other components are mixed in at the elevated temperature. For all examples, the compositions are allowed to come to room temperature prior to use. After the samples are made, they are placed into a container. The consumer preference for taste is tested by allowing a consumer to dip a disposable lip gloss applicator into the container and tasting the sample. The consumer then picks the sample they prefer. The consumer also rates each sample on a scale of −4 to +4 (with −4 being "Dislike Extremely" and +4 being "Like Extremely"). The preferences and ratings for these comparisons are below.

|  | Sample O vs. Sample P | Sample Q vs. Sample R |
| --- | --- | --- |
| Rating | Sample P is preferred over Sample O by 75% of the Panelists Sample O is rated: 0.63 Sample P is rated: 1.75 | Sample R is preferred over Sample Q by 90% of the Panelists Sample Q is rated: 0.9 Sample R is rated: 2.3 |

The above results indicate Sample P is preferred over and rated higher than Sample O. Specifically, Sample P, with R1/R2/R3/R4 ratios of 1/2/2/4, is preferred over and rated higher than Sample O with R1/R2/R3/R4 ratios of 1/25/25/50.

The above results also indicate that Sample R is strongly preferred over and rated much higher than Sample Q. Specifically, Sample R, with R1/R2/R3/R4 ratios of 1/2/2/4, is strongly preferred over and rated much higher than Sample Q with R1/R2/R3/R4 ratios of 1/25/25/50.

Examples 35S-T

|  | S % | T % |
| --- | --- | --- |
| Petrolatum | 98.5 | 90.0 |
| Saccharin | 0.3 | 2 |
| Mint | 0.6 | 4 |
| Menthol | 0.6 | 4 |
|  | 100.0 | 100.0 |
| R1 | 1.00 | 1.00 |
| R2 | 2.00 | 2.00 |
| R3 | 2.00 | 2.00 |
| R4 | 4.00 | 4.00 |

To make the above examples S and T, the petrolatum is heated to about 70° C. and the other components are mixed in at the elevated temperature. For all examples, the compositions are allowed to come to room temperature prior to use. After the samples are made, they are placed into a container. The consumer preference for taste is tested by allowing a consumer to dip a disposable lip gloss applicator into the container and tasting the sample. The consumer then picks the sample they prefer. The consumer also rates each sample on a scale of −4 to +4 (with −4 being "Dislike Extremely" and +4 being "Like Extremely"). The preferences and ratings for these comparisons are below.

|  | Sample S vs. Sample T |
| --- | --- |
| Rating | Sample T is preferred over Sample S by 80% of the Panelists Sample S is rated: 0.5 Sample T is rated: 1.8 |

The above results indicate Sample T is preferred over and rated higher than Sample S. Specifically, Sample T, with a total Saccharin+Mint+Menthol level of 10% [and R1/R2/R3/R4 ratios of 1/2/2/4], is preferred over and rated higher than Sample S with total Saccharin+Mint+Menthol level of 1.5% [and the same R1/R2/R3/R4 ratios of 1/2/2/4].

Test Methods

To measure the instant viscosity ratio for a given material, for example RS or PS, one calculates the ratio of the material's viscosity at room temperature (25° C.) to its viscosity at an elevated temperature (40° C.), using the following procedure:

Equipment:
  Ares Strain-Controlled Rheometer
  25 mm permanent parallel plates
Method:
  1. Load 25 mm parallel plates onto an Ares rheometer.
  2. Zero the normal force.
  3. Zero the gap @ 25° C. (i.e. room temperature).
  4. Apply the sample of the material to the bottom plate in a semi circular motion moving across the plate. There should be enough specimen such that when a gap of 2.177±0.005 mm is reached and excess is trimmed, the specimen extends evenly to all edges of the plate with no gaps present.
  5. Adjust the Gap using the following procedure:
    Click on set gap icon. Set command gap position to 2.55 mm.
    Set the Max Force Allowed to 100 g.
    Click on set Gap.
    Trim sample with plastic cover slide.
    Set the command gap position to 2.177 mm, Max Force Allowed=100 g.
    Click on set Gap.
    Trim sample with plastic cover slide.
    Set command gap position to 2.147 mm. Max Force Allowed=100 g.
    Click on set Gap.
    Do Not Trim Sample.
    Final Gap should read 2.147±0.005 mm
    Allow the temperature to equilibrate to 25° C.
    Record the Gap and the Axial Force in test notes along with any observations made.
    Start Experiment
  6. Start test:
    Method is a Step Rate (Transient) test that runs the following procedure:
      i. Applies a rate of 0/s for 1 s (a 1 s delay)
      ii. Applies a rate of 5/s for 5 s
    Result should be a curve of Viscosity vs. Time
  7. Record the peak viscosity (aka "Instant Viscosity") of this curve.
  8. Repeat steps 1-7 for the material at 25° C.—a minimum of three times
  9. Repeat steps 1-7 for the material at 40° C.—a minimum of three times
  10. Calculate the average value of the Instant Viscosity for the material at 25° C., and separately at 40° C.
  11. Finally, calculate
    "Instant Viscosity Ratio"=(Average Instant Viscosity for the material at 40° C.)/(Average Instant Viscosity for the material at 25° C.).

For embodiments in which the denture care composition is an article, the dry tack of the article can be measured by the following method: 1. remove the article from the package material; 2. place the article on the palate-portion of a dry, acrylic upper-denture with the teeth facing downward; 3. apply pressure with fingers for about 3 to 10 seconds; 4. thereafter remove finger pressure; 5. then invert the denture with the teeth facing upward. In one embodiment the article demonstrates dry tack if: i. The article does not stick to fingers during steps 1-2, ii. Leaves little or no residue on the fingers in steps 3-4, and iii. In step 5, the article does not fall off of the denture, once inverted, for at least about 10-30 seconds, or at least about 1 minute.

In another embodiment the article demonstrates dry tack if: i. The article does not stick to fingers during steps 1-4, and ii. In step 5, the article does not fall off of the denture, once inverted, for at least about 10-30 seconds, or at least about 1 minute.

In another embodiment the article demonstrates dry tack if in step 5, the article does not fall off of the denture, once inverted, for at least about 10-30 seconds, or at least about 1 minute For embodiments in which the composition is an article, the modulus G' of the article can be measured by the following procedure:

a. Load a sample disc of 8 mm diameter and 0.67 mm thickness onto an ARES rheometer using a parallel plate fixture (at least 8 mm in diameter) with a compressive force of 500 grams. If the sample is flowable a sufficient amount of material is used to fill the 1 mm gap on a 25 mm diameter parallel plate fixture;

b. Set strain to be 0.02%;

c. Measure G' at a sweep of frequencies including 1 Hz;

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it will be obvious to those skilled in the art that various changes and modifications may be made without departing from the spirit and scope of the invention. It is therefore intended to cover in the appended claims all such changes and modifications that are within the scope of the invention.

What is claimed is:

1. A denture care composition comprising:
   (a) a denture care active including one or more sweeteners, sensates or flavors; wherein
      a. the ratio of the weight of sensates to the weight of flavors in the composition is from about 0.5 to about 2.0;
      b. the ratio of the weight of flavors to the weight of sweeteners in the composition is from about 1.0 to about 4.0;
      c. the ratio of the weight of sensates to the weight of sweeteners in the composition is from about 1.0 to about 4.0; and/or
      d. the ratio of the combined weight of sensates and flavors to the weight of sweeteners in the composition is from about 0.4 to about 40; and
   (b) one or more water insoluble carriers;
   wherein the composition is bioerodible, not a denture adhesive, substantially free of polybutene with a molecular weight of about 300 to about 3000 when the composition is not an article, and is applied to dentures.

2. The composition of claim 1, further comprising a denture care active selected from the group consisting of anti-calculus agents, fluoride ion sources, stannous ion sources, whitening agents, antimicrobial agents, anti-plaque agents, anti-inflammatory agents, nutrients, antioxidants, anti-viral agents, anti-fungal agents, analgesic and anesthetic agents, H-2 antagonists, fragrances, sensates, pigments, dyes, lakes, colorants, flavors, sweeteners, and mixtures thereof.

3. The composition of claim 2, further comprising a denture care active that is an antimicrobial agent.

4. The composition of claim 1, wherein the water insoluble carrier is a water insoluble thermoplastic component selected from the group consisting of rubber, natural wax, synthetic wax, polyvinyl chloride, nylon, fluorocarbon, polyurethane prepolymer, polyethylene, polystyrene, polypropylene, cellulosic resins, acrylic resins, petrolatum, polyvinyl acetate and mixtures thereof.

5. The composition of claim 1, wherein the water insoluble carrier is petrolatum.

6. The composition of claim 1, further comprising a viscosity index improver and/or wherein the water insoluble carrier is a viscosity index improver.

7. The composition of claim 1, wherein the water insoluble carrier is selected from the group consisting of mineral oil, natural and synthetic oils, fats, silicone, silicone derivatives, dimethicone, silicone resins, hydrocarbons, hydrocarbon derivatives, essential oils, caprilic/capric triglycerides, corn, soy bean, cottonseed, castor, palm oil, coconut oil, vegetable oils, animal oils, fish oil, oleic acid, and mixtures thereof.

8. The composition of claim 1, wherein the water insoluble carrier is from about 50% to about 99%, by weight of the composition, and wherein the denture care active is from about 0.1% to about 50%, by weight of the composition.

9. The composition of claim 1, wherein the water insoluble carrier comprises from about 50% to about 99%, by weight of the composition, petrolatum and/or microcrystalline wax, and the denture care active is from about 0.1% to 50%, by weight of the composition.

10. The composition of claim 1, wherein the water insoluble carrier comprises from about 70% to about 99%, by weight of the composition, petrolatum and/or microcrystalline wax and from about 1% to 25%, by weight of the composition, carboxymethyl cellulose, and wherein the denture care active is from about 0.1% to about 30%, by weight of the composition.

11. The composition of claim 1, wherein the one or more water insoluble carriers is hydrophobic and/or the composition is nonaqueous.

12. The composition of claim 1, wherein the composition comprises a uniform mixture of the one or more denture care actives and the one or more water insoluble carriers.

13. The composition of claim 1, wherein the composition is a cream, paste, gel, liquid, strip, wafer, article, or mixture thereof.

14. The composition of claim 1, wherein the water insoluble carrier is selected from the group consisting of microcrystalline wax, paraffin wax, bees wax, petrolatum, mineral oil, polybutene, silicone, natural oil, synthetic oil, polyethylene, and combinations thereof.

15. The composition of claim 1, wherein the composition does not comprise an effective amount of mucoadhesive components and/or components that increase the retention of the denture in the oral cavity.

16. The composition of claim 1, wherein the composition adheres to the surfaces of the denture.

17. A method of delivering denture care actives to the oral cavity of a denture wearer, said method comprising the steps of:
   a. applying the composition of claim 1 to the surface of a denture; and
   b. applying the denture to the oral cavity;
   wherein the length of time the composition remains in the oral cavity is from application to about 8 hours.

18. A method of delivering denture care actives to a denture, said method comprising the steps of:
   a. applying the composition of claim 1 to the surface of a denture; and
   b. immersing the denture in water.

19. The composition of claim 1, wherein at least one denture care active is spray-dried, encapsulated, and/or at least partially contained in a hydrophilic matrix.

20. The composition of claim 1, comprising a sweetner selected from the group consisting of saccharin, sucralose, Rebiana, xylitol, aspartame, Acesulfame K, mono ammoniated glycyrrhizinate, and mixtures thereof.

21. The composition of claim 1, comprising a sensate selected from the group consisting of menthol; 3-1-menthoxypropane-1,2-diol, menthyl lactate; N,2,3-trimethyl-2-isopropylbutanamide; N-ethyl-p-menthan-3-carboxamide ; N-(4-cyanomethylphenyl)-ρ-menthanecarboxamide, and combinations thereof.

22. The composition of claim 1, further comprising monoalkyl phosphate.

* * * * *